United States Patent [19]

Schultz

[11] Patent Number: 4,891,125
[45] Date of Patent: Jan. 2, 1990

[54] REFERENCE ELECTRODE AND METHOD OF MAKING IT

[75] Inventor: Steven G. Schultz, Winthrop Harbor, Ill.

[73] Assignee: Abbott Laboratories, Abbott Park, Ill.

[21] Appl. No.: 336,944

[22] Filed: Apr. 12, 1989

[51] Int. Cl.⁴ ............................................. G01N 27/30
[52] U.S. Cl. ................................ 204/435; 128/635; 264/267
[58] Field of Search ................ 204/435, 403, 415, 416; 264/267; 128/635

[56] References Cited

U.S. PATENT DOCUMENTS

| | | | |
|---|---|---|---|
| 4,233,136 | 11/1980 | Spaziani et al. | 204/435 X |
| 4,366,038 | 12/1982 | Kearney et al. | 264/267 X |
| 4,496,512 | 1/1985 | Marsoner et al. | 264/267 |
| 4,519,973 | 5/1985 | Cahalan et al. | 264/267 |

Primary Examiner—G. L. Kaplan
Attorney, Agent, or Firm—John W. Cornell; Thomas D. Brainard

[57] ABSTRACT

A miniaturized reference electrode includes a dielectric thermoplastic cup having a cavity to hold a reference liquid solution and having a sample contacting orifice at one end. A membrane comprising cellulose acetate and a solvent capable of exerting a solvent action on the sidewalls of the cup orifice is drop deposited in the orifice and cured in situ. The resulting membrane extends across the orifice and is interdigitatedly anchored to the orifice sidewalls. The reference electrode further includes an Ag/AgCl screw-in electrode machined from silver rod extending into and hermetically sealing the cup cavity. A reference liquid fill solution having a chloride ion and potassium ion concentration similar to that found in the samples to be tested and the storage soak solution is provided to minimize drift of reference potential. The miniature reference electrode is intended for use with a miniaturized ISE half cell in a test cartridge on a centrifugal clinical analyzer to determine electrolyte concentrations in fluid samples.

7 Claims, 2 Drawing Sheets

REFERENCE ELECTRODE AND METHOD OF MAKING IT

BACKGROUND OF THE INVENTION

The present invention relates to apparatus and methods for determining electrolyte concentrations in a patient sample. More particularly, it relates to a new and improved miniaturized reference electrode for use in combination with a miniature ion selective electrode in a multi-chambered sample cartridge for making electrolyte determinations using centrifugal clinical analyzer equipment.

This application is related to the following commonly assigned applications being filed concurrently herewith: Ser. No. 337,007, relating to a miniature ION SELECTIVE ELECTRODE AND METHOD OF MAKING SAME, to be used with the miniature reference electrode of this invention; and two continuations in part from U.S. application Ser. No. 196,120, filed May 25, 1988, the first, Ser. No. 337,011 describing a TWO PART TEST CARTRIDGE FOR CENTRIFUGE, and the second Ser. No. 363,943 relating to digital electronic aspects of an APPARATUS FOR MEASURING ELECTROLYTES. Each of these above-identified applications are specifically incorporated herein by reference.

Methods for determining the electrolyte concentration in a sample fluid utilizing ion selective electrodes are known. Typically the measurement apparatus includes, an electrometer connecting a pair of chemical half cells including a first ISE sensor half cell and a reference electrode half cell. For determining potassium concentration of a patient serum sample, for example, the sensor half cell includes an electrode and membrane separated by a fill solution of known potassium concentration. The membrane has an affinity for potassium ions and is typically made from an ion sensitive polypeptide composition, e.g. valinomycin in polyvinyl chloride. When the sensor half cell membrane is brought in contact with the fluid sample, the sensor membrane forms very specific complexes with the potassium ions in the sample. A voltage or potential is developed across the membrane that is proportional to the unknown potassium concentration in the sample. Following the Nernst Equation, by knowing the ion concentration on the fill solution side of the sensor membrane and measuring the potential across the sensor membrane, it is possible to calculate the unknown ion concentration on the opposite or sample side of the membrane.

A reference half cell is similar in its construction to the ISE sensor half cell except that the reference membrane is generally formed of a non-ion specific material, typically ceramic or glass frit. The reference half cell is designed to maintain a relatively constant potential and is used to complete the electrical circuit through the unknown sample.

Centrifugal type clinical analyzers are used to perform a variety of clinical tests on a fluid sample, such as whole blood, plasma or serum. In accordance with the above-identified pending application, the analyzer uses centrifugal force to separate whole blood; measure reagents and plasma volumes; and to complete all steps required for spectrophotometric analysis. The system is based on a two dimensional centrifugation process in which a multi-chambered cartridge or cassette containing the sample and liquid reagents is centrifuged at 500 G's in two planes oriented at right angles to one another. The plastic multi-chambered test cartridge itself is of a very small size having dimensions generally similar to an ordinary credit card size and being between ¼ to ½ of an inch in thickness.

A major object of this invention is to provide an ion-selective electrode system including an ISE sensor half cell and a reference half cell which are incorporated into the small sized cassette for use on the centrifugation analyzer equipment. To satisfy this object, considerable miniaturization for the ISE sensor electrode, and the reference electrode, had to be achieved.

Conventional reference electrodes have generally been of two popular types including the $Hg/Hg_2Cl_2$ (calomel) type and the $Ag/AgCl$ type. These reference electrodes form a stable electrochemical half cell when placed in contact with a known reference solution of known chloride ion concentration.

A key problem in making a reference electrode is to provide both an electrical connection and a liquid junction between a reference liquid solution in the reference electrode and the sample being tested. The interface between the liquids should be sufficiently permeable to permit appropriate ion migrations on both sides of the junction with a low characteristic junction resistance. The liquid junction must also provide a practical barrier to fluid flow to prevent sample contents from entering into the electrode itself and thereby changing the composition of the reference fill solution and therefore the reference potential. Prior art reference electrodes have used glass frits and fibers to form the liquid junction interface between the reference solution and the sample.

A major problem with the glass frit liquid junction barriers is that contamination of the reference liquid fill solution often occurs due to permeability. Changes or drift in the reference half cell potential may result which require that the half cell be re-calibrated often. Attempts to overcome the potential drift have included a circulating fresh reference liquid solution through the reference half cell on the electrode side of the reference membrane. Expensive and elaborate equipment modifications are required to provide a flow system for the reference fill solution.

In the present design context, size constraints built into the test cartridge for use in the centrifugation equipment determined that a miniaturized reference electrode was needed, having a liquid junction orifice of approximately 0.020 of an inch in diameter.

A major design difficulty was to develop a membrane that could physically separate the sample from the reference fill solution but which would form an electrical connection and liquid junction therebetween characterized by low reference junction resistance to provide improved electrochemical sensing with respect to the solution.

In this design context, glass frit or fiber membranes were poor candidates for filling such a small orifice at the liquid junction of the reference electrode. A number of other micro porous filter membranes were considered to form the reference membrane, such as nylon filters, but it was difficult to determine how these membranes could be glued, tacked or welded into the reference electrode orifice. Moreover, many prior art membranes were unable to restrict flow or permeability by an amount sufficient to minimize the sample contamination of the reference cell fill fluid without disadvantageously increasing the minimum junction resistances of the reference half cell.

It is known from U.S. Pat. No. 3,333,626, for example, that various cellulose acetate membrane forming compositions may be used for making a cast planar membrane having appropriate membrane characteristics for kidney dialysis. More particularly, the '626 patent describes a method for making advantageous screen membranes by: mixing cellulose acetate in a major organic solvent; adding a second diluent solvent; and adding a metal salt to provide a substantially monophasic solution. The solution is cast onto a polished plane surface to form a thin film. Thereafter, the solvents are removed from the composition by evaporation at a temperature less than 50° C. During the evaporation, a microphase separation of the two solvent based systems occurs, providing a cellulose acetate web having discreet metal ions or salt particles positioned or imbedded therein. Upon full evaporation and drying of the film membrane, the metal salts are removed from the film by contacting the film with a solvent for the metal salt thereby removing it from the porous membrane into solution. This leaves a plurality of micropores in the cellulose acetate web. The '626 patent does not describe or suggest a method for securely attaching the membrane made therein to an orifice of the type presented in a reference electrode, much less a tiny orifice of about 0.020 of an inch in diameter, as required for the miniature reference electrodes contemplated herein. The overall miniature reference electrode half cell for use in the centrifugal clinical analyzer and test cartridge was required to be approximately the size of a ¼ to ½ inch screw.

In order to overcome the deficincies in prior art reference electrodes, it is an object of the present invention to provide a miniaturized reference electrode adapted for use in a test cartridge or cassette device used in a centrifugation clinical analyzer.

It is another object of the present invention to provide a new and improved miniaturized reference electrode including a low impedence liquid junction membrane capable of providing an electrical connection and a liquid junction between a reference liquid solution in the electrode and a solution to be tested.

It is a further object of the present invention to provide a new and improved reference electrode liquid junction membrane which does not permit, or substantially limits contamination of the reference liquid solution in use.

It is another object of the present invention to provide a method for making a new and improved reference electrode membrane and for attaching the reference membrane to the reference electrode half cell.

SUMMARY OF THE INVENTION

In accordance with these and other objects, the present invention provides a new and improved miniature reference electrode for providing both electrical connection and a liquid junction between the reference liquid solution and a solution to be tested comprising:

cup means including a cavity to hold the reference liquid solution, having a sample contacting orifice at one end and an opposed second end, said orifice being defined by a peripheral sidewall;

a membrane comprising cellulose acetate extending across said orifice and interdigitatedly anchored to said peripheral sidewall;

means for applying a generally fixed cotrol potential to said reference liquid solution; and means for hermetically closing the second open end of said cavity.

In accordance with the present invention, the cup means comprises a dielectric thermoplastic material and preferably an acrylic thermoplastic material.

The reference electrode is a miniature screw in type silver/silver chloride electrode. The reference liquid fill solution comprises from about 1 to 10 mM KCl in from about 50 to about 150 mM saline (NaCl in $H_2O$). When the sample to be tested comprises a blood product, e.g., whole blood, plasma or serum, the fill solution is preferably similar to the chloride and potassium ion concentrations generally found in blood. More particularly, the preferred fill solution comprises about 7 millimolar potassium chloride in 100 mM saline.

In accordance with another aspect of this invention the new and improved miniature reference electrode is made by drop-depositing an amount of a liquid junction membrane forming composition comprising cellulose acetate and a first polar organic solvent which is capable of dissolving not only the cellulose acetate, but which also is capable of partially dissolving or softening the thermoplastic material of the cup means, into the sample contacting orifice. The drop of membrane forming composition acts on the peripheral sidewalls of the orifice as the solvents are evaporated, to provide irregularities in the side wall surface or indentations which may be filled by the developing web of the cellulose acetate solution. Upon final evaporation and curing, the membrane is firmly interdigitatedly anchored into the side wall of the orifice. Thereafter, the membrane may be conditioned by contacting it with water, for example, to remove the metal ions thereby forming micropores therein to provide an improved liquid junction. The reference half cell is intended for use in the ion selective electrode apparatus and method described in the above-identified related applications for determining the electrolyte concentration of the patient sample.

In accordance with the present invention the reference electrode liquid junction membrane-forming composition comprises:

(a) from about 0.3% about 5.0% by weight cellulose acetate having an acetyl content of from about 25% to about 50%;

(b) from about 70% to about 90% by weight of a first polar organic solvent, said first solvent being capable of dissolving (a) and exerting a solvent action against the thermoplastic material of said cup means;

(c) from about 1% to about 5% by weight of an inorganic metal salt selected from the group consisting of lithium, sodium, magnesium, calcium, zinc, potassium, aluminum and copper salts;

(d) from about 5% to about 15% by weight of a $C_1$ to $C_{10}$ alcohol capable of dissolving (c) and miscible in (b); and (e) optionally, from about 1% to about 5% by weight of a flexibility improving agent selected from $C_5$–$C_{10}$ cyclic hydrocarbons; $C_5$–$C_{10}$ cyclic mono hydric alcohols and $C_1$–$C_4$ alkyl esters of aliphatic and aromatic carboxylic acids, based upon the weight of the overall composition.

The preferred reference electrode membrane composition in accordance with the present invention comprises acetone as the first polar organic solvent, calcium chloride as the metal salt; methanol as the second solvent and dimethyl phthalate as the flexibility enhancing agent, added within the ranges specified above.

Other objects and advantages of the present invention will become apparent from the following Detailed Description of the invention taken in conjunction the drawings in which:

DETAILED DESCRIPTION OF THE PREFERRED EMBODIMENT

Figure 1:
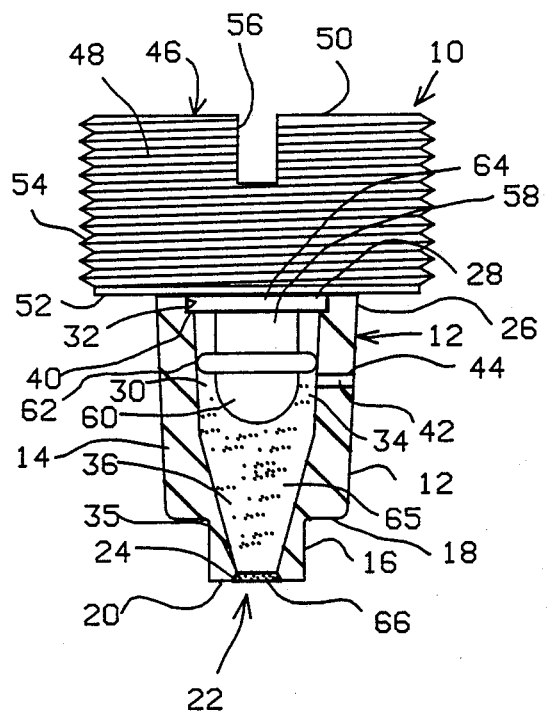
FIG. 1 is an elevated cross-sectional view of the new and improved miniature reference electrode assembly 10 of the present invention.
Figure 2:
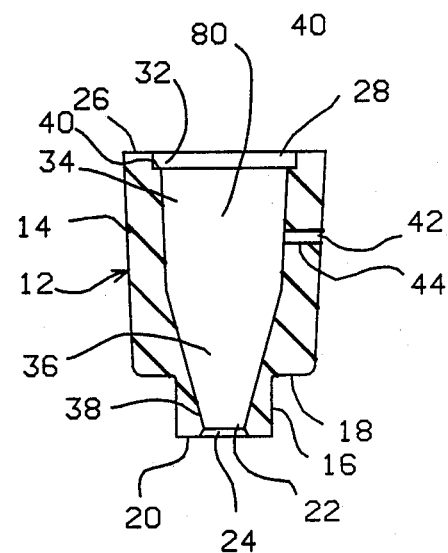
FIG. 2 is an elevated sectional view of the cup means of the new and improved miniature reference electrode assembly of the invention.
Figure 3:
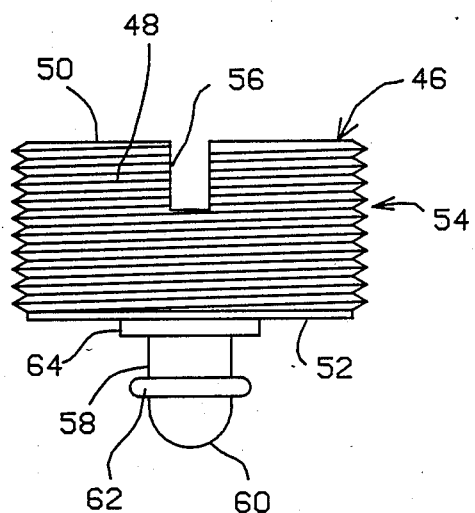
FIG. 3 is an elevated sectional side view of the screw in Ag/AgCl electrode for use in the reference electrode assembly of this invention.

Referring now to FIGS. 1-3, the new and improved reference electrode assembly, generally referred to by reference numeral 10, is shown.

As shown in FIGS. 1-2, reference electrode assembly 10 comprises a cup means 12 having a generally tubular configuration including a main body portion 14, a narrower forwardly projecting portion 16, and a stepped shoulder 18 therebetween. The outer surfaces of body portion 14 and forward portion 16 are each tapered inwardly to facilitate proper seating of cup means 12 in a stepped socket defined in the test cartridge (not shown). The front end 20 of forward portion 16 includes a narrow sample contacting orifice or opening 22 having an outwardly flared lead in 24 as shown. The opposed upper or rearward end 26 of main body portion 14 also includes an enlarged opening 28. Cup means 12 further includes a cavity 30 extending between orifice 22 and opening 28 having an enlarged electrode-receiving portion 32, a central portion 34 of generally constant internal diameter and a tapered transition portion 36. Transition portion 36 extends between central portion 34 and orifice 22 and at the lower portions thereof defines the inner peripheral sidewall 38 of orifice 22. The junction between electrode receiving portion 32 and central portion 34 defines a seating shoulder 40. A reference fill solution opening 42 and fill tube 44 extend through the sidewall of main body portion 14 to permit a reference liquid fill solution to be introduced into cavity 30.

Cup means 12 is formed of a dielectric thermoplastic material and may comprise any moldable thermoplastic which is soluble, partly soluble or exhibits poor solvent resistance for polar organic solvents. Illustrative examples include without limitation acrylic based thermoplastics, thermoplastic polyesters and thermoplastic polycarbonates. Acrylic thermoplastics are preferred.

Referring now to FIGS. 1 and 3, reference electrode assembly 10 further includes a screw in type of Ag/AgCl electrode 46. Electrode 46 includes a generally cylindrical head 48 extending between a rear end or surface 50 and a front end or surface 52. An array of external threads 54 are defined on the outer surfaces of head 48 which are adapted to threadingly engage an array of internal threads provided in the socket of the test cartridge. A tool-receiving groove 56 for receiving the blade of a screw driver is defined in rear surface 50 to facilitate engagement of the reference electrode assembly 10 into the test cartridge socket. The test cartridge socket includes a conductive layer extending into the array of internal threads for electrically engaging the external threads 54 of electrode 46 thereby electrically connecting reference electrode 46 to the other circuit members.

Electrode 46 further includes a cylindrical shaft portion 58 projecting concentrically and forwardly from front surface 52 of head 48 to a rounded free end 60. A first annular projection 62 extends outwardly from shaft 58 at a point spaced from free end 60 adapted to be slidingly engaged within central portion 34 of cavity 30 to ensure that free end 60 is centrally located within cavity 30. A second annular projection 64 extends outwardly from shaft 58 adjacent head 48. Projection 64 has a diameter larger than the diameter of projection 62 and is adapted to be seatingly engaged in the enlarged electrode receiving portion 32 of cavity 30 and to rest against seating shoulder 40. This further serves to locate free end 60 in the central portion of cavity 30 at an appropriate depth and aids in hermetically sealing the cavity 30 during assembly.

Screw in reference electrode 46 is made by machining silver rod stock to define the electrode configuration in accordance with well known machining methods. Thereafter, the electrode must be chloridized in a manner to be more fully explained below. As presently designed, the head 48 of reference electrode 46 measures about ¼ of an inch in diameter and about ⅛ of an inch in height.

In accordance with the present invention, reference electrode assembly 10 further includes a reference liquid junction membrane 66 extending completely across orifice 22 and interdigitatedly anchored to inner peripheral sidewall 38 of orifice 22 to provide both an electrical connection and a liquid junction between the reference fill solution 68 provided in cavity 30 and a patient sample to be tested. The reference membrane 66 of the invention is formed in situ by evaporative curing of a new and improved membrane-forming composition.

More particularly, the new and improved reference membrane forming composition of the present invention generally comprises cellulose acetate and a micropore-forming metal salt, each dissolved in its own preferential solvent. The co solvents are miscible and prior to evaporation can for a single phase solution. Upon evaporation of the solvents, both the cellulose acetate and the metal salt precipitate or "salt out" at varying rates and thereby cure to form a thin layer membrane including imbedded metal ions which may be subseguently dissolved away in a solvent for the metal salt, such as lower alkyl alcohols or water.

It has been discovered that the best adhesion of the membrane 66 to peripheral sidewalls 38 of orifice 22, is obtained if the solvent for cellulose acetate is also capable of eroding the surfaces of sidewalls 38 at orifice 22. Without wishing to be bound by any particular theory, it is believed that the solvent action on the cup means 12 creates surface irregularities including indentations. The cellulose acetate solution fills these irregularities and fingersoout into surface indentatiohs and thereafter cures in this locked or interdigitated relationship with the sidewalls 38 to promote adhesion of membrane 66 to orifice 22. Adhesion or anchoring of the membrane 66 is especially important in the present centrifugal analyzer design context because the calibrator and sample solutions are driven through test cartridge channels past orifice 22 under considerable centrifugal forces. Experimentation has suggested that solvents for cellulose acetate which also affect the thermoplastic material from which the cup means is formed, exhibit improved anchoring over solvents to which the thermoplastic material has good solvent resistance.

After experimentation, it has been discovered that a composition useful for forming the reference liquid junction membrane comprises:

(a) from about 0.3% to about 5.0% by weight cellulose acetate having an acetyl content from about 25% to about 50%;

(b) from about 70% to about 90% by weight of a first polar organic solvent, said first solvent being capable of dissolving (a) and being capable of party dissolving or softening the thermoplastic material of the cup means;

(c) from about 1% to 5% by weight of an inorganic metal salt selected from the group consisting of lithium, sodium, magnesium, calcium, zinc, potassium, aluminum and copper salts;

(d) from about 5% to about 15% by weight of a $C_1$ to $C_{10}$ alcohol capable of dissolving (c) and miscible with (b); and (e) optionally but preferrably, from about 1% to about 5% by weight of a flexibility improving agent selected from $C_5$-$C_{10}$ cyclic hydrocarbons; $C_5$-$C_{10}$ monohydric alcohols and lower $C_1$-$C_4$ alkyl esters of aliphatic and aromatic carboxylic acids, based upon the weight of the overall composition.

Membrane compositions comprising from about 0.3% to about 1% by weight of (a); from about 80% to 90% by weight of (b); from about 2.5% to about 4.0% by weight of (c); from about 5% to about 10% of (d); and from about 1% to 2% by weight of (e) based upon the weight of the overall composition are preferred.

Each of the ingredients for making the membrane forming composition are commercially available from a number of sources.

Polar organic solvents for use as component (b) herein include acetone, tetrahydrofuran and methylene chloride. The preferred solvent for use as component (b) herein, when the cup means is a thermoplastic acrylic material, is acetone.

The metal salts referred to in component (c) may include any anion, however halogen ions, such as chloride and bromide ions, and perchlorate ions are preferred because of their solubility in alcohols. The preferred metal salt for use herein as component (c) is $CaCl_2 2H_2O$.

The preferred $C_1$-$C_{10}$ alcohol solvent (d) is methanol, although ethanol, cyclopentanol and cyclohexanol, as well as other members of the group, may also be used.

The flexibility enhancing agents for use as component (e) may include cyclohexane, cyclohexanol, cyclopentanol, alkyl esters of benzoic acid and phthalic acid alkyl diesters, to name but a few. The preferred enhancing agent for use as component (e) is dimethyl phthalate.

The membrane forming composition may be prepared by dissolving component (a) in solvent (b) by agitating for several hours or until completely dissolved. A second solution of metal salt (c) in alcohol (d) is prepared. The two solutions are mixed and the flexibilizer or toughening agent (e) is added.

In accordance with the method of the present invention, the new and improved reference electrode assembly 10 is prepared by forming and anchoring the reference liquid junction membrane 66 in situ across sample contacting orifice 22.

Figure 4C:
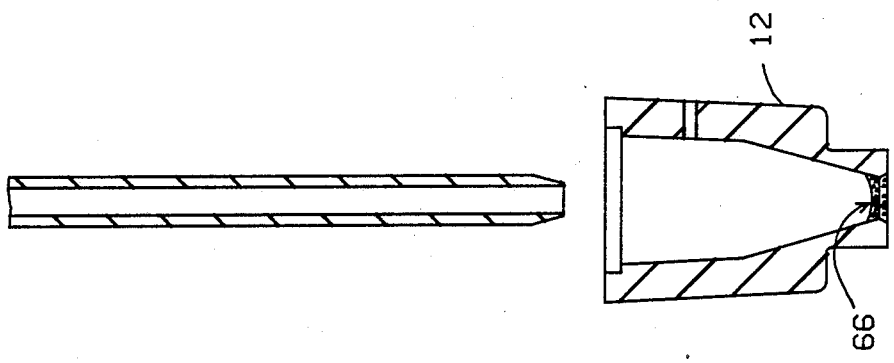
FIGS. 4a-4c schematically illustrate the steps for forming the new and improved reference liquid junction membrane of the reference electrode of the invention.
Figure 4B:
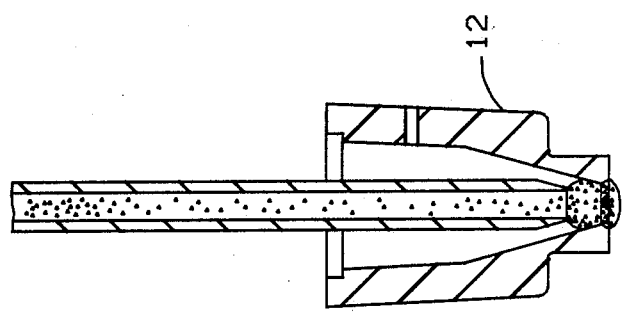
Figure 4A:
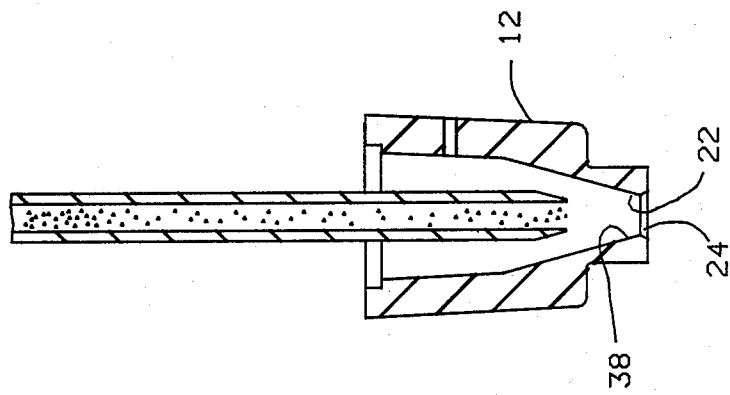

Referring now to FIGS. 4a–4c, membrane 66 is formed by placing cup means 12 in a holder (not shown) with orifice 22 down. A portion of the membrane forming composition is drawn into a 0.75 $\mu l$ pipette. The pipette is introduced into cavity 30 of cup means 12 as shown in FIG. 4a. Thereafter, the membrane-forming composition is dispensed at a moderate, even speed until a small ball or droplet extends from the flared entry 24 to orifice 22, as shown in FIG. 2b. The pipette is withdrawn and the solution is allowed to evaporate and cure at room temperature for a period of at least about one hour.

Upon curing, the membrane 66 forms a flat slightly concave layer extending on opposed upper and lower sides of orifice 22 as shown in FIG. 4c. The membrane is thereafter soaked in de ionized water or alcohol to remove the metal ions from the cellulose acetate to form the micropores and is thereafter permitted to dry.

The screw in reference electrode 46 is chloridized to form a Ag/AgCl reference electrode prior to assembly with the membraned cup means prepared above. The electrode 46 may be chloridized by first cleaning the silver parts twice in acetone followed by rinsing with de ionized water three times. A solution containing 0.3 grams of NaCl, 0.3 grams $NaH_2PO_4 \cdot H_2O$ and 5 mls of household bleach is prepared and the cleaned electrodes are soaked in the solution with mild agitation for about 8 minutes. The chloridized Ag/AgCl electrodes are removed from the solution, rinsed four times with de ionized water and are permitted to dry.

Next, a commercially available epoxy adhesive composition such as EPOTEK BF113 is applied by hand using a syringe and needle to the front end 52 of electrode 46 adjacent second projection 64. Additional epoxy may be dispensed along shaft 58 in the groove formed between projections 62 and 64, if desired. Electrode 46 is then inserted into cavity 30 until second projection 64 rests on shoulder 40 and the upper end 26 of cup means 12 contacts the adhesive applied on front electrode surface 52. The intermediate assembly including the cup means 12, membrane 66 and inserted electrode 46 is then inverted to rest on the rear end surface 50 of the electrode 46 for a period of about 15 hours or overnight, sufficient to cure the epoxy adhesive and to form an hermetic seal at the enlarged opening 28 between electrode 46 and cup means 12.

The assembled reference electrode 10 is thereafter filled with a reference liquid fill solution 68. The cavities 30 of reference electrode assemblies 10 are filled by placing them into a vacuum chamber equipped with a fill solution supply connected to the chamber by means of a valve. As mentioned above, the fill solution comprises 7 mM KCl solution in 100 mM saline. The vacuum chamber is evacuated with a vacuum pump for a period of at least about 10 minutes. Thereafter, the fill solution 68 is added to the chamber through the valve until each of the electrode assemblies are completely covered with fill solution. The fill solution is permitted to de gas in the chamber for a period of about 20 to 30 minutes.

The chamber is slowly re pressurized to one atmosphere causing the fill solution 68 to enter cavity 30 through the fill solution opening 42 and tubing 44 and to completely fill the cavity 30. A heated probe is then introduced into opening 42 to fuse the opening and tubing 44 shut to hermetically seal the filled cavity 30.

The completely assembled reference electrode 10 is stored in a soaking solution also preferably comprising 7 mM KCl in 100 mM saline which is substantially the same as the reference fill solution 68. The new and improved membrane of the reference electrode of the present invention substantially prevents contamination of the reference fill solution 68 by contact with a sample solution. For this reason the reference fill solution 68 of the reference electrode assembly 10 does not have to circulated or replenished from a source outside cavity 30.

In addition, the reference fill solution 68 and the storage solution for the reference electrodes were selected to be substantially the same in ion concentration, especially for chloride ion, as human blood, which usually comprises the sample fluid being tested in the test cartridge for electrolyte concentration. This limits any drift in the reference potential for the reference electrode assembly 10 over time. If sample fluids other than blood is used, the reference fill solution and the storage soak solution should also be selected to be approximately within the range of chloride ion concentrations generally found in that sample fluid.

Moreover, in accordance with the test centrifugation methods described in the above-mentioned concurrently filed applications, when the reference electrode 10 is screwed into its test socket, the electrode is contacted by a sequence of solutions including a calibrator fluid, the test sample and another calibrator fluid to compensate for any drift in reference potential and to verify integrity of the membrane before and immediately after the sample has been tested.

Further details for making and using the new and improved miniature reference electrode assembly 10 of the present invention may be obtained from the following working example.

EXAMPLE 1

Two membrane forming compositions were prepared in accordance with the methods set forth above from the following ingredients:

| Components, % by weight | A* | 1** |
|---|---|---|
| (a) Cellulose acetate (39.4% acetyl content, available from KODAK) | 8.0 | 0.5 |
| (b) Tetrahydrofuran (anhydrous, 99.9%, available from ALDRICH) | 82.0 | — |
| (b) acetone | — | 87.3 |
| (c) $CaCl_2$ (anhydrous) | 3.0 | — |
| $CaCl_2 \cdot 2H_2O$, (available from Fisher) | — | 3.3 |
| (d) methanol (HPLC grade, available from FISHER) | 7.0 | 7.3 |
| (e) Dimethyl phthalate | — | 1.6 |
| | 100% | 100% |

*Within the scope of U.S. Pat. No. 3,883,626
**This invention

Each of the membrane forming compositions was used to form membranes in situ in accordance with the procedures described above in connection with FIGS. 4a–4c. A large number of duplicate reference electrode assemblies were assembled according to the methods set forth above to produce filled and hermetically sealed electrode assemblies such as assembly 10 shown in FIG. 10.

The reference electrodes were evaluated using a YSI Model 35 Conductance Meter to determine the conductance of the reference electrode liquid junction membranes. Both the membrane of composition A and Example 1 exhibited conductances of between 1 to 50 $\mu$MHOS.

The reference electrode membranes were evaluated for adhesion to the orifice and durability by positioning them in a test cartridge apparatus including a base provided with a stepped socket with internal threads for receiving the reference electrode assemblies and including a flow passage extending past the orifice of the inserted electrodes. Adhesion was measured by lifetime experiments by running the test cartridges equiped with the prepared reference electrode assemblies on the VISION® CENTRIFUGE SYSTEM, available from ABBOT LABORATORIES. Further description of the test cartridge and the centrifugal analyzer are set forth in the above cited applications, which are specifically incorporated herein by reference. The reference electrode assemblies and the test cartridges were subjected to 1,000 cycles on the VISION® SYSTEM to simulate about 300 electrolyte assays. Thereafter, the reference electrode conductances were again measured in the YSI Model 35 Conductance Meter. The measured conductance of the membranes formed from EXAMPLE 1 remained substantially unchanged from the previous values obtained prior to flow testing. The membranes formed from Example A generally exhibited a marked increase in conductance indicating that the membrane had perforated or pulled away from the orifice of the electrode cup.

Although the present invention has been described with reference to a preferred embodiment, modifications or changes may be made therein by those skilled in this art. Instead of using cellulose acetate, other web forming porous membrane-forming polymeric materials may be substituted, such as, for example, cellulose nitrate, polycarbonate, nylon and other cellulosic polymers. All such obvious modifications may be made herein without departing from the scope and spirit of the present invention, as defined by the appended claims.

We claim:

1. A miniature reference electrode providing both electrical connection and a liquid junction between a reference liquid solution and a solution to be tested comprising:

cup means including a cavity to hold the reference liquid solution having a sample contacting orifice at one end and an opposed open second end, said orifice being defined by a peripheral sidewall;

a membrane comprising cellulose acetate extending across said orifice and interdigitatedly anchored to said peripheral sidewall;

means for applying a generally fixed control potential to said reference liquid solution; and means for hermetically closing the second open en of said cavity.

2. A miniature reference electrode as in claim 1, wherein said cup means comprises a dielectric thermoplastic material.

3. A miniature reference electrode as in claim 2 wherein said cellulose acetate membrane is formed in situ from a composition comprising:

(a) from about 0.3% to about 5.0% by weight cellulose acetate having an acetyl content of from about 25% to about 50%;
(b) from about 70% to about 90% by weight of a first polar organic solvent, said first solvent being capable of dissolving (a) and at least partially dissolving the thermoplastic material of said cup means;
(c) from about 1% to about 5% by weight of an inorganic metal salt selected from the group consisting of lithium, sodium, magnesium, calcium, zinc, potassium, aluminum and copper salts;
(d) from about 5% to about 15% by weight of a $C_1$ to $C_{10}$ alcohol capable of dissolving (c) and miscible in (b); and
(e) optionally, from about 1% to about 5% of a flexibility improving agent selected from $C_5$–$C_{10}$ cyclic hydrocarbons; $C_5$–$C_{10}$ cyclic monohydric alcohols and lower $C_1$–$C_4$ alkyl esters of aliphatic and aromatic carboxylic acids, based on the weight of the overall composition.

4. A miniature reference electrode as in claim 1, wherein said cup means comprises an acrylic thermoplastic material.

5. A miniature reference electrode as in claim 1 wherein said means for applying a generally fixed control potential comprises an electrode disposed in said cavity.

6. A miniature reference electrode as in claim 5, wherein said electrode comprises a Ag/AgCl electrode and said reference liquid solution comprises from about 1.0 to about 10.0 mM KCl in from about 50 to about 150 mM saline.

7. In a miniature reference electrode half-cell, a method for making a reference liquid junction membrane for providing an electrical connection and a liquid junction between a reference liquid solution and a solution to be tested comprising:

(a) providing a cup means of a dielectric thermoplastic material including a cavity to hold the reference liquid solution having a sample contacting orifice at one end and an opposed second end, said orifice being defined by a peripheral sidewall;
(b) preparing a liquid junction membrane composition by
 (1) dissolving about 0.3% to about 5.0% by weight of cellulose acetate having an acetyl content of from about 25% to about 50% in 70% to 90% by weight of a first polar organic solvent capable of at least partially dissolving said thermoplastic material;
 (2) dissolving from about 1% to about 5% by weight of an inorganic metal salt selected from Li, Na, Mg, Ca, Zn, K, Al, Cu salts in from about 5% to about 15% by weight of a second solvent comprising a $C_1$ to $C_{10}$ alcohol;
 (3) mixing the solutions of step (1) and (2) together;
 (4) thereafter, optionally adding from about 1% to about 5% by weight of a flexibility improving agent selected from $C_5$–$C_{10}$ cyclic hydrocarbons; $C_5$–$C_{10}$ cyclic monohydric alcohols and lower $C_1$–$C_4$ alkyl esters of aliphatic and aromatic carboxylic acids, based on the weight of the overall composition, to the mixture of step (3) to form the membrane composition;
(c) depositing a drop of said liquid junction membrane composition through said cavity and into said orifice in contact with the peripheral sidewall;
(d) curing and interdigitatedly anchoring said membrane to said orifice by permitting the solvents to evaporate until membrane formation is substantially complete; and
(e) thereafter contacting said membrane with a solvent for said metal salt to create micropores therein by removal of said metal salt from the membrane.

* * * * *

UNITED STATES PATENT AND TRADEMARK OFFICE
CERTIFICATE OF CORRECTION

PATENT NO. : 4,891,125

DATED : January 2, 1990

INVENTOR(S) : Steven G. Schultz

It is certified that error appears in the above-identified patent and that said Letters Patent is hereby corrected as shown below:

In Column 10, Line 29-30, delete "EXAMPLE 1" and substitute therefor, "Example 1".

Signed and Sealed this

Fourteenth Day of May, 1991

Attest:

HARRY F. MANBECK, JR.

*Attesting Officer*  *Commissioner of Patents and Trademarks*